(12) United States Patent
Itonaga et al.

(10) Patent No.: US 10,119,962 B2
(45) Date of Patent: Nov. 6, 2018

(54) SAMPLE ANALYSIS DEVICE AND CAPTURING METHOD FOR EXOSOMES

(71) Applicant: JVC KENWOOD CORPORATION, Yokohama-shi, Kanagawa (JP)

(72) Inventors: Makoto Itonaga, Yokohama (JP); Shingo Yagyu, Yokohama (JP); Yuichi Hasegawa, Yokohama (JP); Koji Tsujita, Yokohama (JP); Masayuki Ono, Yokohama (JP)

(73) Assignee: JVC KENWOOD CORPORATION, Yokohama-Shi, Kanagawa (JP)

( * ) Notice: Subject to any disclaimer, the term of this patent is extended or adjusted under 35 U.S.C. 154(b) by 445 days.

(21) Appl. No.: 14/875,015

(22) Filed: Oct. 5, 2015

(65) Prior Publication Data
US 2016/0033486 A1     Feb. 4, 2016

Related U.S. Application Data

(63) Continuation of application No. PCT/JP2014/058960, filed on Mar. 27, 2014.

(30) Foreign Application Priority Data

Apr. 9, 2013   (JP) ................. 2013-081122
Mar. 24, 2014  (JP) ................. 2014-059623

(51) Int. Cl.
*G01N 33/53*     (2006.01)
*G01N 33/543*    (2006.01)
*G01N 33/536*    (2006.01)
*G01N 33/487*    (2006.01)

(52) U.S. Cl.
CPC ....... *G01N 33/5302* (2013.01); *G01N 33/487* (2013.01); *G01N 33/536* (2013.01); *G01N 33/54313* (2013.01); *G01N 33/54373* (2013.01)

(58) Field of Classification Search
CPC ................................. G01N 33/54373
USPC ....................................... 422/82.11
See application file for complete search history.

(56) References Cited

U.S. PATENT DOCUMENTS 4,647,544 A * 3/1987 Nicoli ............... G01N 21/4788
                                                250/461.1
2012/0058492 A1* 3/2012 Lozupone ............ G01N 33/567
                                                435/7.23
2012/0288408 A1   11/2012 Ono et al.

FOREIGN PATENT DOCUMENTS

| CN | 102317778 A | 1/2012 |
| JP | 9-159673 A | 6/1997 |
| JP | 2004-173681 A | 6/2004 |
| JP | 2006-38567 A | 2/2006 |

(Continued)

OTHER PUBLICATIONS

European Search Report dated Sep. 23, 2016 issued in corresponding European Application No. 14 78 2305.

(Continued)

*Primary Examiner* — Christopher L Chin
(74) *Attorney, Agent, or Firm* — Nath, Goldberg & Meyer; Jerald L. Meyer; Stanley N. Protigal

(57) ABSTRACT

A recessed portion and a protruding portion arranged periodically are formed on a base portion. In the recessed portion, an antibody that binds to an antigen existing on a surface of each exosome to be detected is immobilized and then caused to bind to the exosomes. The width of the protruding portion is smaller than the average particle diameter of the exosomes.

4 Claims, 11 Drawing Sheets

(56) References Cited

FOREIGN PATENT DOCUMENTS

JP     2012-255772 A     12/2012
WO     2010/065765 A2    6/2010

OTHER PUBLICATIONS

Kim, et al, "Noble Polymeric Surface Conjugated with Zwitterionic Moieties and Antibodies for the Isolation of Exosomes from Human Serum", Bioconjugate Chemistry, vol. 23, pp. 2114-2120, 2012.
Koga, et al., "Purification, Characterization and Biological Significance of Tumor-derived Exosomes", Anticancer Research vol. 25, pp. 3703-3708, 2005.
Thery, et al., "Exosomes: Composition, Biogenesis and Function", Nature Reviews Immunology, pp. 569-579, 2002.
Tsujita, et al., "Ultrahigh-Sensitivity Biomarker Sensing System Based on the Combination of Optical Disc Technologies and Nanobead Technologies", Japanese Journal of Applied Physics, vol. 52, No. 9S2, pp. 09LB02-1, 2013.
Official Action dated Mar. 6, 2017 issued in corresponding the counterpart Japanese Application No. 2014-059623.
Office action issued in Chinese application No. 201480029913.4 dated Oct. 25, 2016.

* cited by examiner (a)

(b)

(a)

(b)

SAMPLE ANALYSIS DEVICE AND CAPTURING METHOD FOR EXOSOMES

CROSS REFERENCE TO RELATED APPLICATION

This application is a Continuation of PCT Application No. PCT/JP2014/058960, filed on Mar. 27, 2014, and claims the priority of Japanese Patent Application No. 2013-081122, filed on Apr. 9, 2013, and Japanese Patent Application No. 2014-059623, filed on Mar. 24, 2014, the entire contents of all of which are incorporated herein by reference.

BACKGROUND

The present disclosure relates to a sample analysis device to analyze exosomes secreted from various types of cells and a capturing method for the exosomes.

Detection of diseases or quantitative analyses of therapeutic effects are widely carried out by detecting and analyzing certain antigens (or antibodies) associated with the diseases as biomarkers. One of substances expected as a new biomarker in recent years is minute membrane vesicles referred to as exosomes.

Exosomes are included in blood, lymph, saliva, urine, breast milk, semen, and the like. Exosomes are approximately spherical in liquid, and the diameters thereof are distributed around 100 nm. An exosome is covered with a lipid bilayer membrane, and various substances, such as membrane proteins, for example, exist in the lipid bilayer membrane. Exosomes have plural names and are also referred to as microvesicles or extracellular vesicles.

SUMMARY

WO2009/092386 (Patent Literature 1) describes detection and analyses of exosomes using immunological measurement (immunoassay). By using the immunological measurement described in Patent Literature 1, exosomes can be detected by recognizing an antibody against membrane proteins serving as an antigen and existing in the lipid bilayer membrane of each exosome. However, the number of membrane proteins varies from one exosome to another, and it is not possible to detect the number of exosomes accurately.

Accordingly, there is a need for a sample analysis device and a capturing method for exosomes which are capable of detecting exosomes with high accuracy. The highly accurate detection of exosomes enables highly accurate quantitative measurement of exosomes.

A first aspect of the embodiments provides a sample analysis device, including: a base portion; a recessed portion which is formed on the base portion and in which an antibody that binds to an antigen existing on a surface of each exosome to be detected is immobilized and then caused to bind to the exosomes; and a protruding portion adjacent to the recessed portion, wherein the recessed portion and the protruding portion are periodically arranged on the base portion, and wherein the protruding portion has a width smaller than an average particle diameter of the exosomes.

A second aspect of the embodiments provides a sample analysis device, including: a base portion; a recessed portion which is formed on the base portion and in which an antibody that binds to an antigen existing on a surface of each exosome to be detected is immobilized and then caused to bind to the exosomes; and a protruding portion adjacent to the recessed portion, wherein the recessed portion and the protruding portion are periodically arranged on the base portion, and wherein the protruding portion has a width smaller than a diameter of beads modifying the exosomes.

Figure 7:
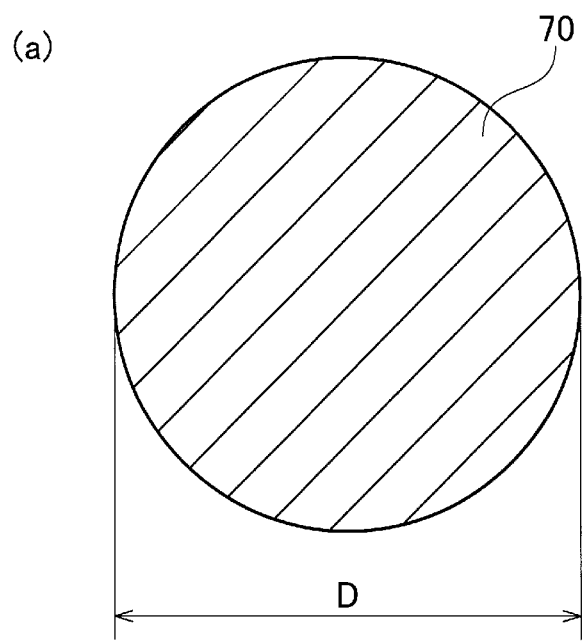
Figure 7:
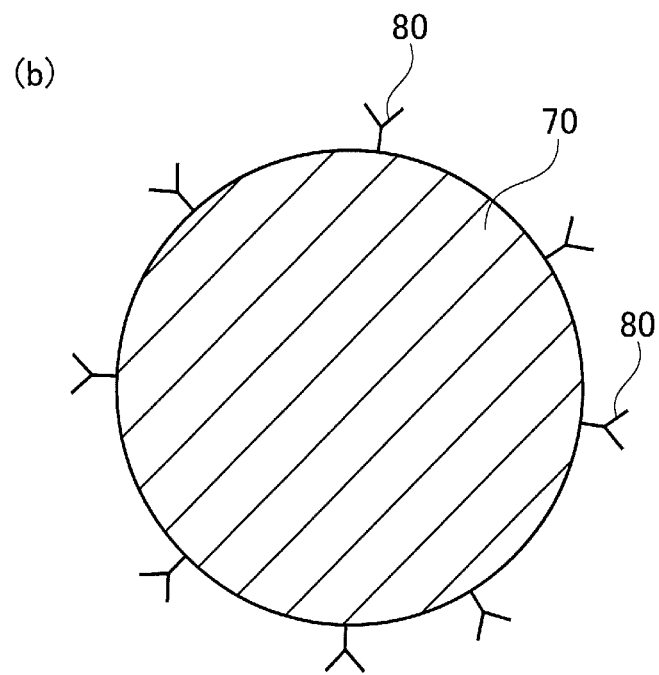

(a) and (b) of FIG. 7 are cross-sectional views illustrating a bead for modifying exosomes.

Figure 8:
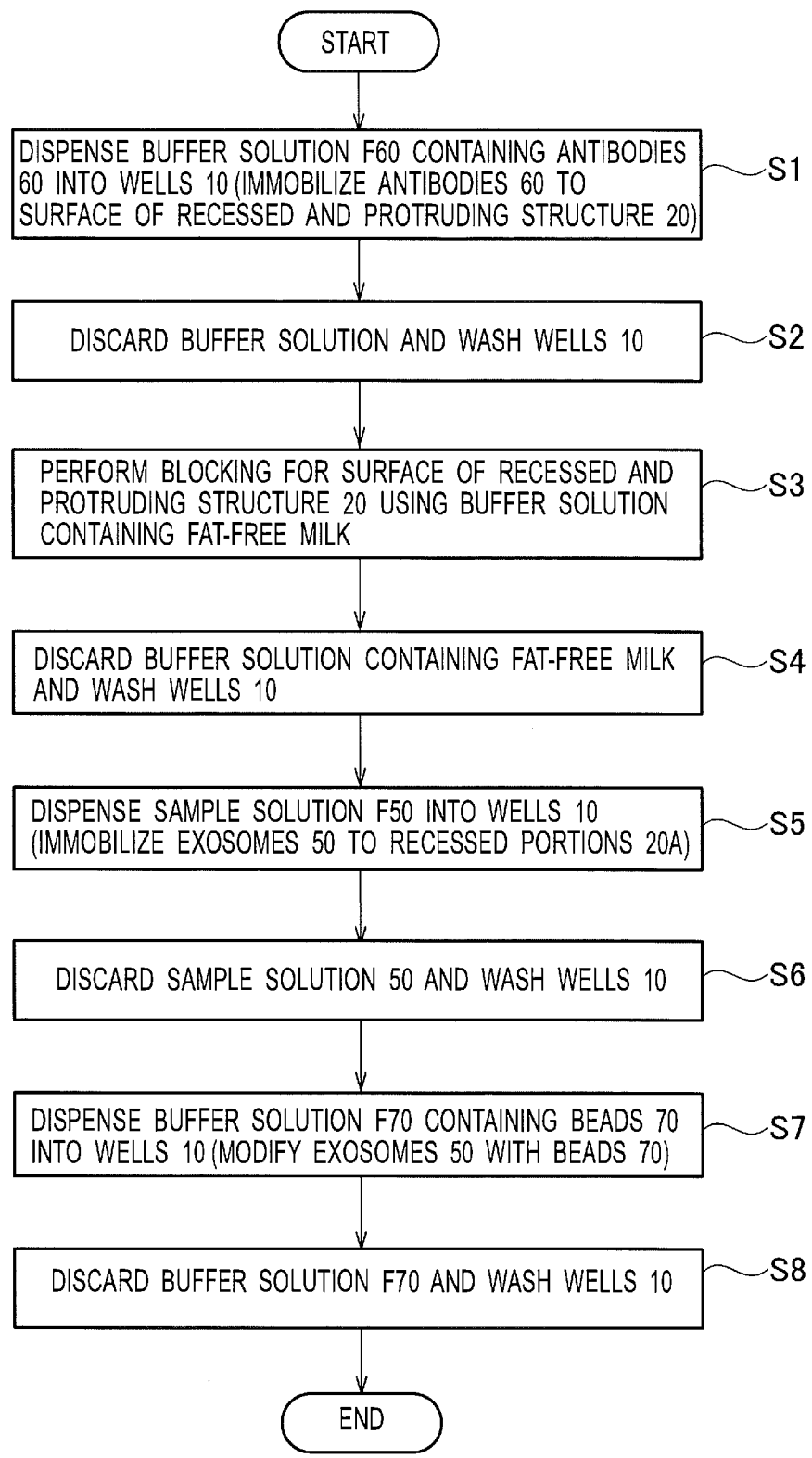

FIG. 8 is a flowchart showing a capturing method for exosomes according to at least one embodiment.

Figure 9:
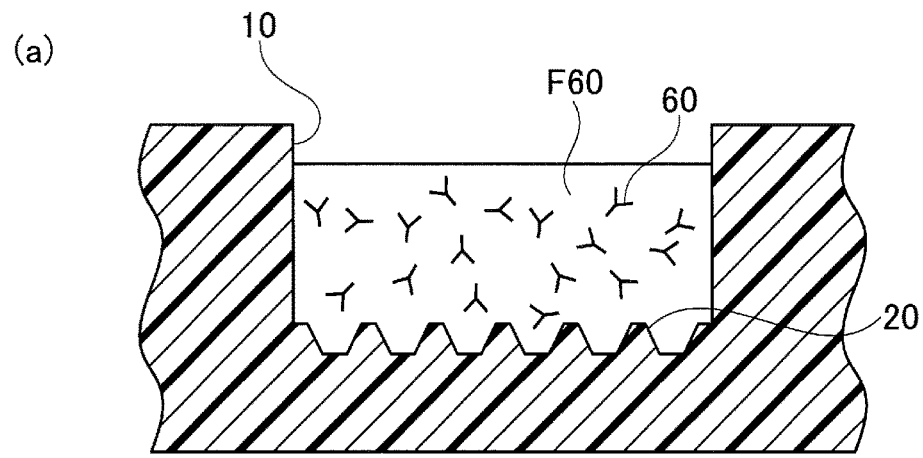
Figure 9:
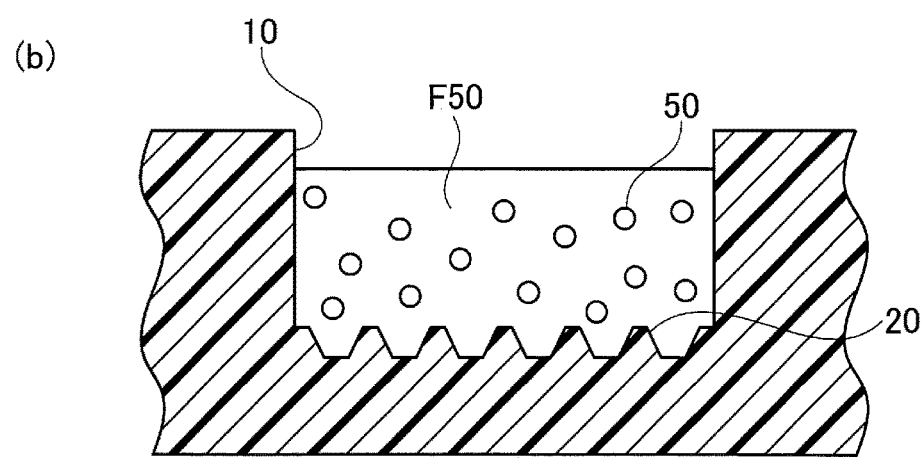
Figure 9:
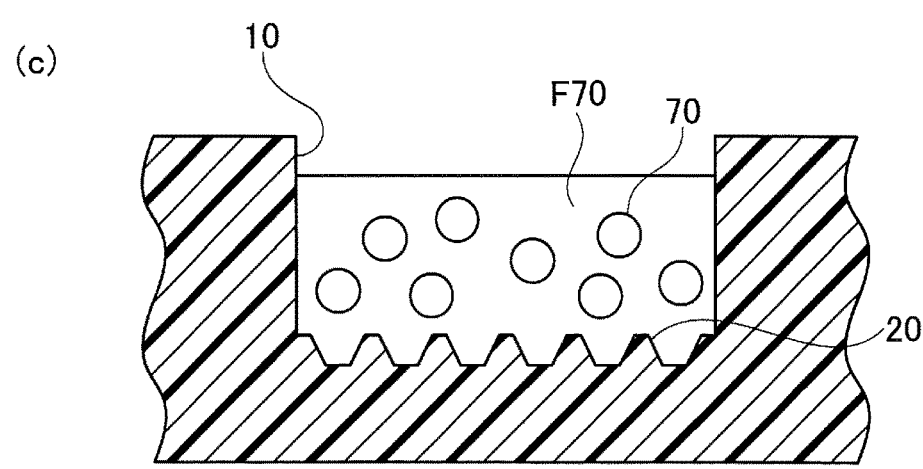

(a) to (c) of FIG. 9 are partial enlarged cross-sectional views for explaining steps executed in the capturing method for exosomes according to the embodiment.

Figure 10:
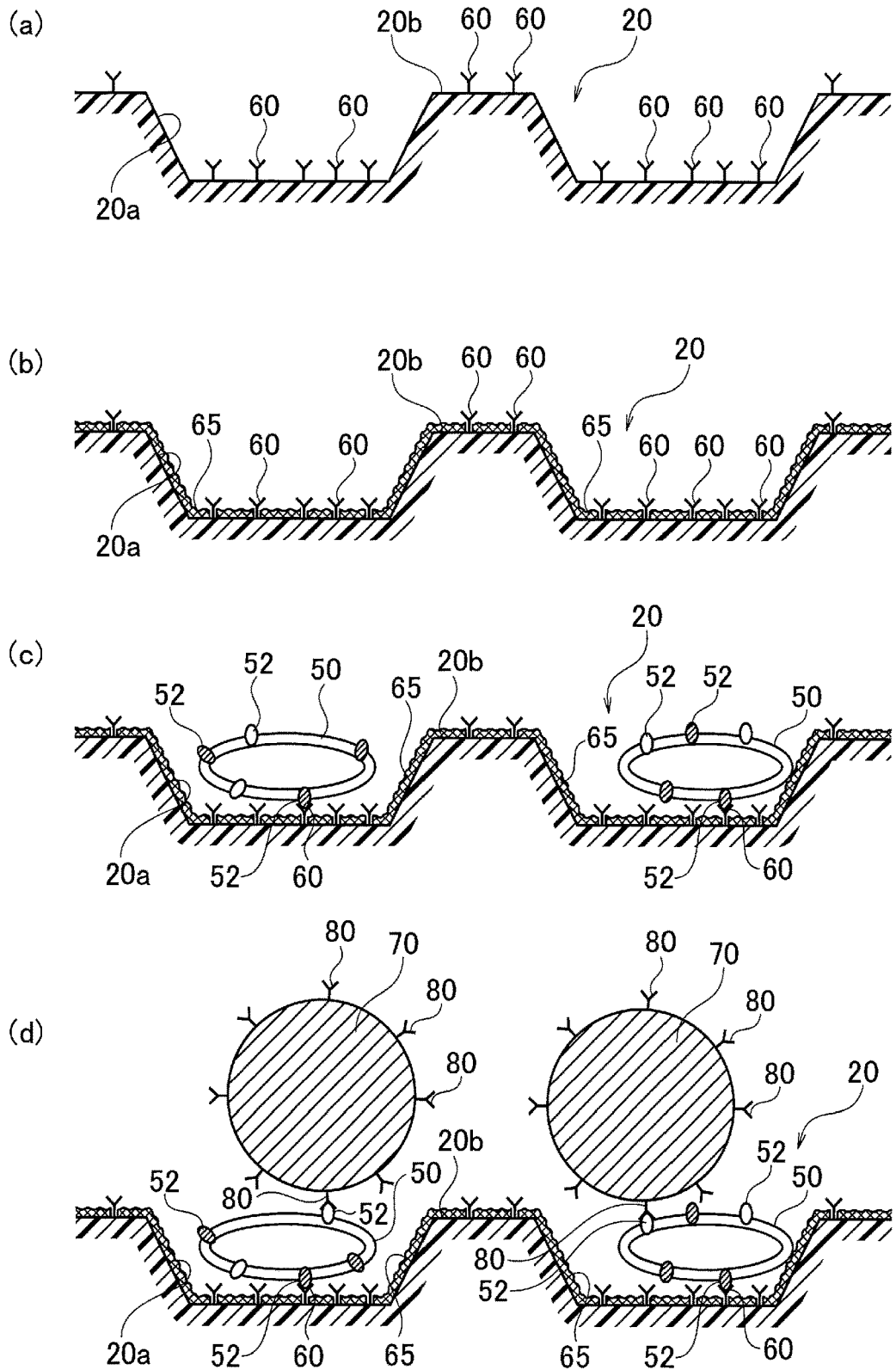

(a) to (d) of FIG. 10 are partial enlarged cross-sectional views of the sample analysis device, schematically illustrating states on the recessed and protruding structure which are caused by the steps executed in the capturing method for exosomes according to the embodiment.

Figure 11:
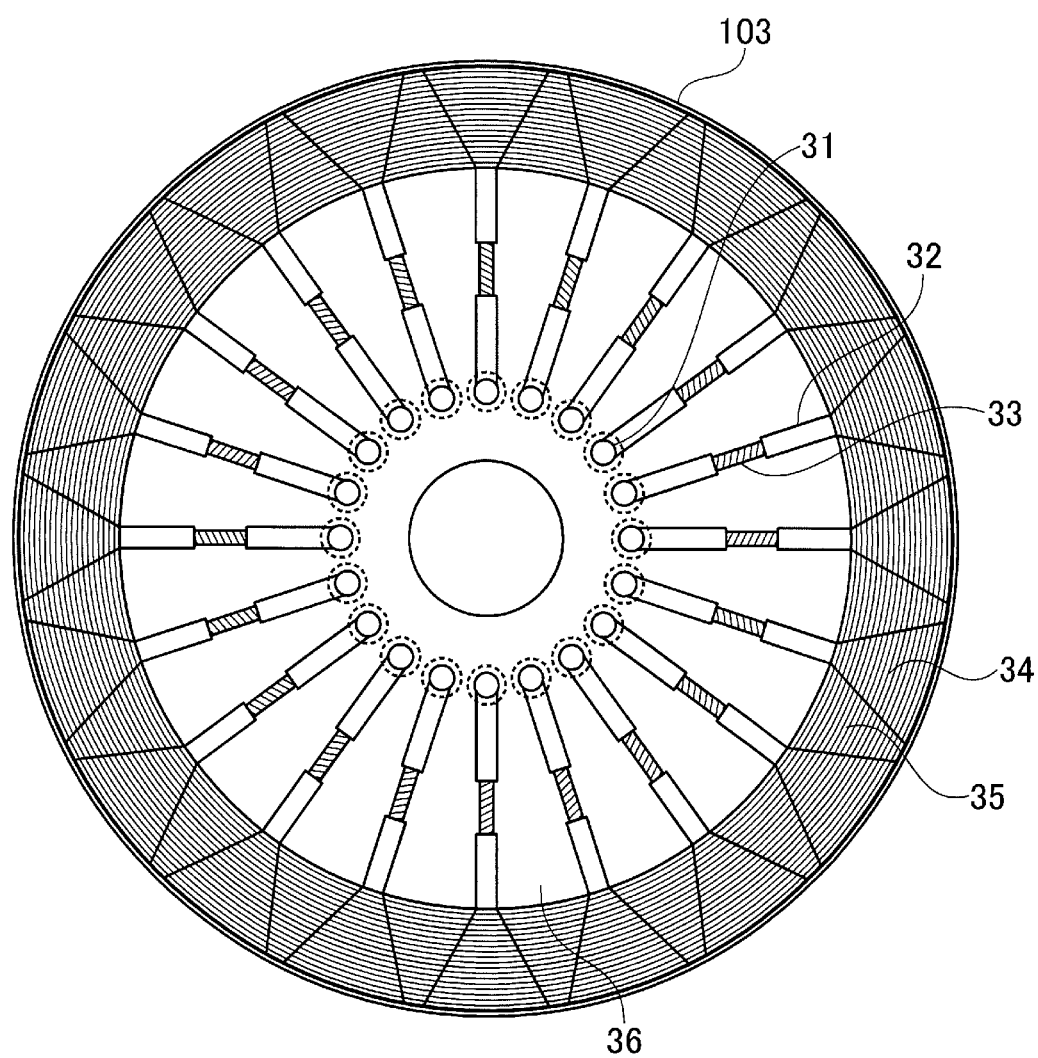

FIG. 11 is a plan view illustrating the sample analysis device according to the third embodiment.

Figure 12:
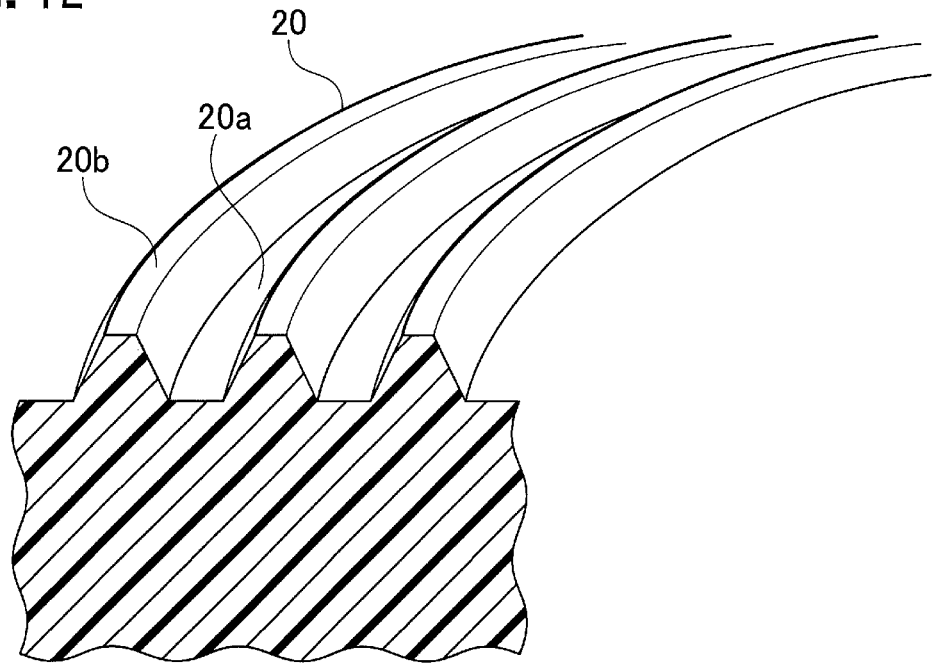
Figure 12:
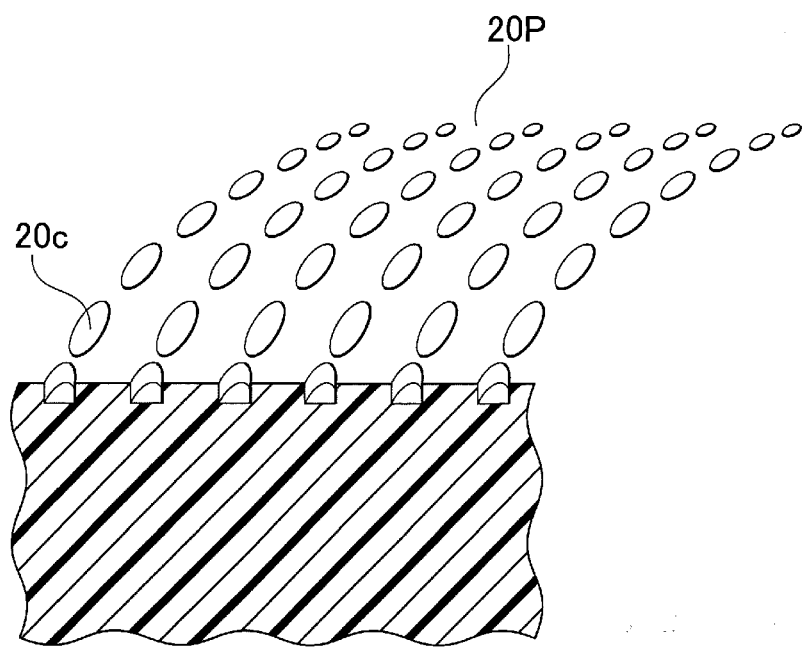

(a) and (b) of FIG. 12 are partial enlarged cross-sectional views of the recessed and protruding structure in the sample analysis device according to the third embodiment.

Figure 13:
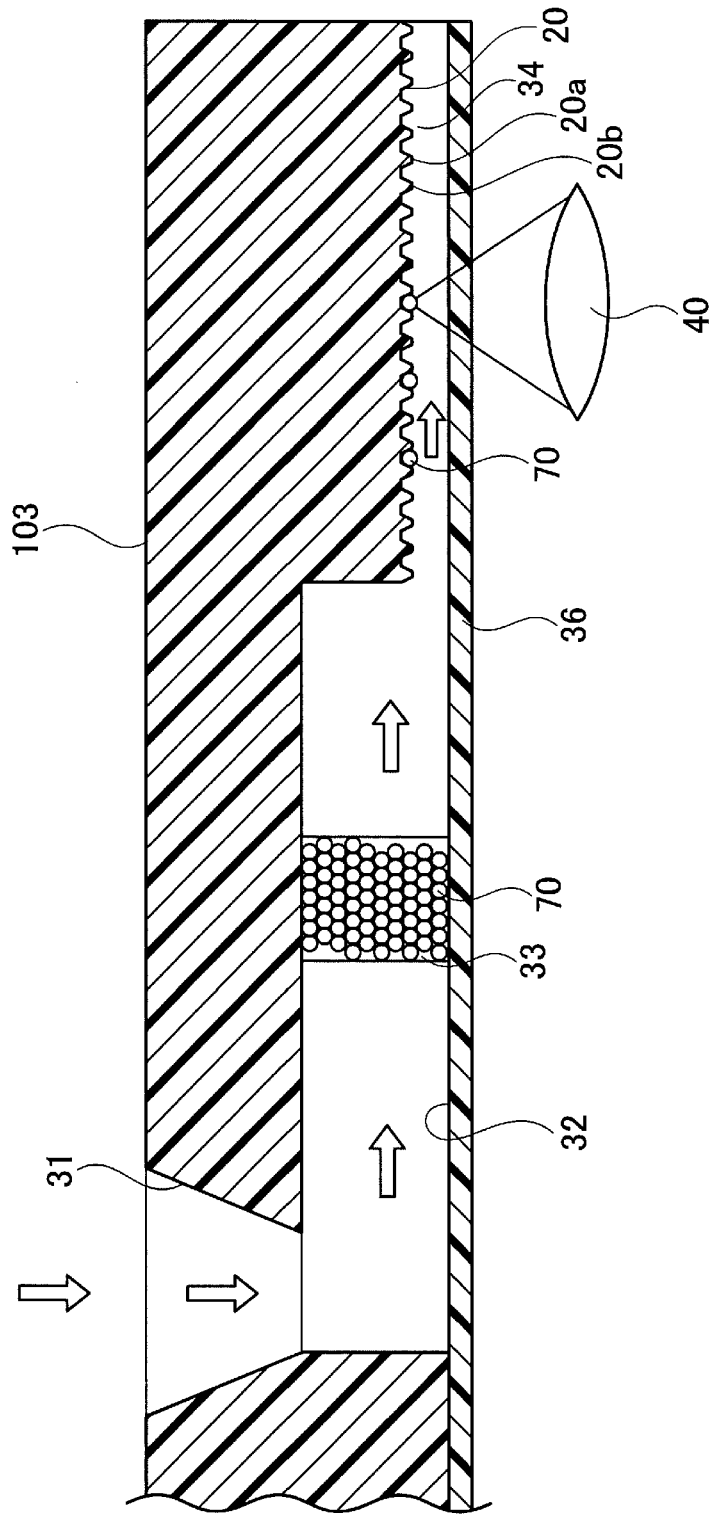

FIG. 13 is a partial cross-sectional view illustrating the sample analysis device according to the third embodiment.

DETAILED DESCRIPTION

Hereinafter, a description is given of a sample analysis device and a capturing method for exosomes of each embodiment with reference to the accompanying drawings.

<Sample Analysis Device According to First Embodiment>

Figure 1:
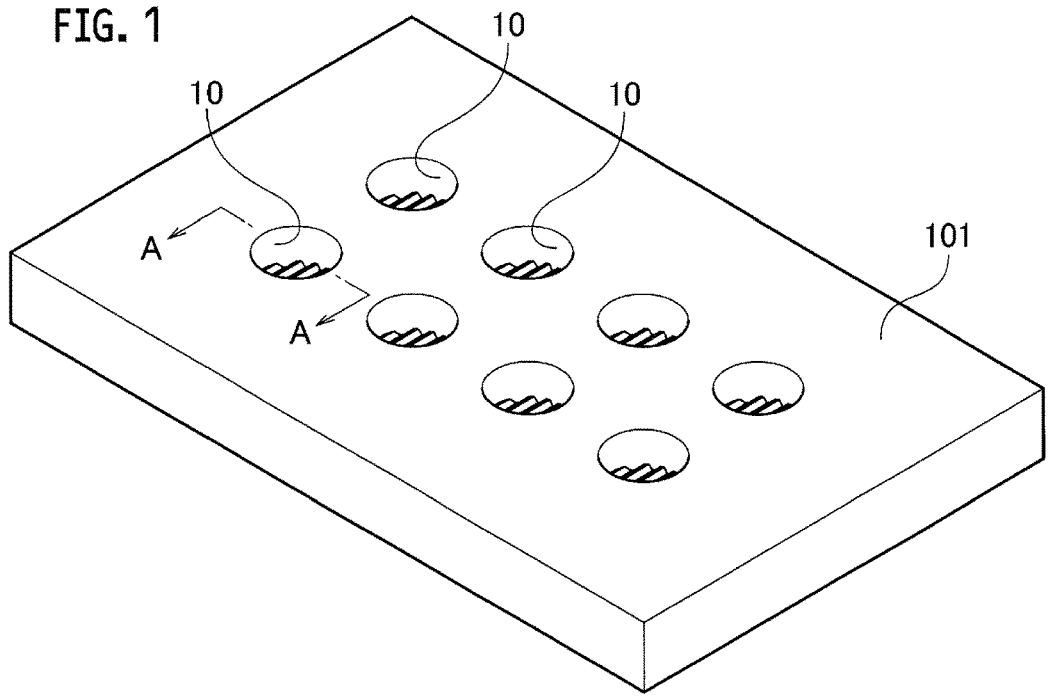
FIG. 1 is a perspective view illustrating a sample analysis device according to the first embodiment.
Figure 2:
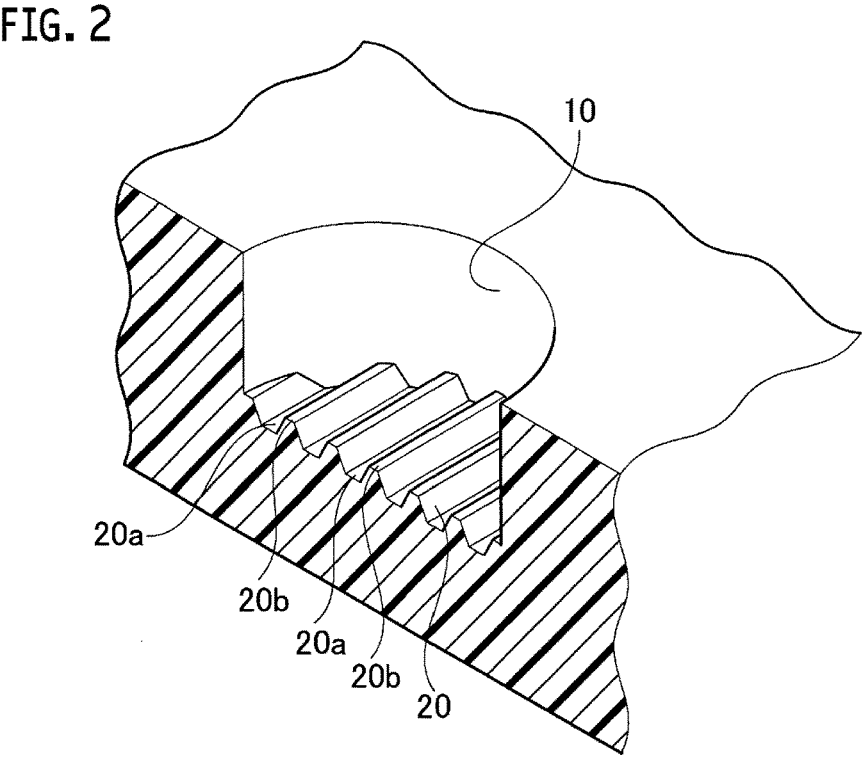
FIG. 2 is a partial enlarged perspective view taken along a line A-A of FIG. 1.
Figure 3:
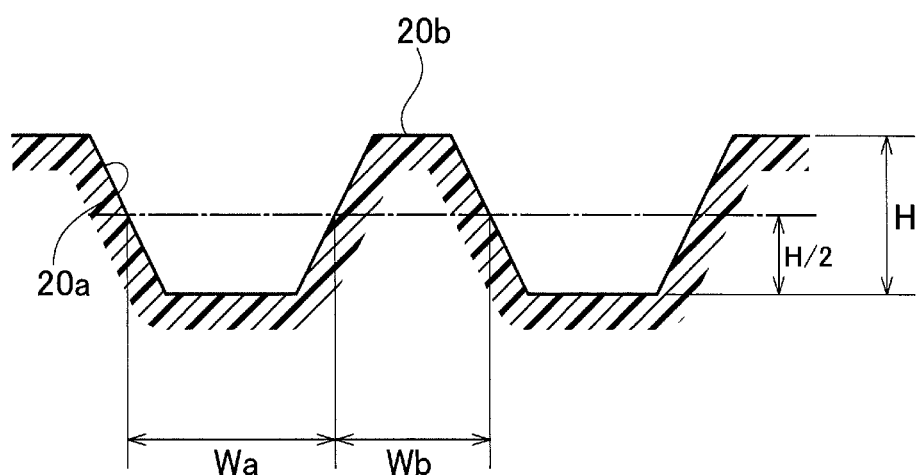
FIG. 3 is an enlarged cross-sectional view illustrating the dimensional profile of the recessed and protruding structure of the sample analysis device according to the first to third embodiments.

Using FIGS. 1 to 3, the configuration of the sample analysis device according to the first embodiment, is described. In FIG. 1, a sample analysis device 101 according to the first embodiment is made of synthetic resin and is rectangular, for example. The outer profile of the sample analysis device 101 is not limited to the rectangular profile and can have any profile.

The sample analysis device 101 can be made of glass, metal, a semiconductor substrate, or the like.

The sample analysis device 101 includes plural wells 10, each of which is a cylindrical recess. In FIG. 1, eight wells 10 are formed in the sample analysis device 101. However, the sample analysis device 101 may include more wells 10 and includes any number of wells 10. The wells 10 are injection portions to which each liquid described later is injected.

The cross section of each well 10 cut in the direction orthogonal to the thickness direction of the sample analysis device 101 is a true circle. The cross-sectional shape of each well 10 may be elliptic or rectangular. However, it is preferable that the cross-sectional shape of each well 10 is a true circle.

FIG. 2 illustrates an enlarged view of a cross-section taken along a liner A-A of FIG. 1. As illustrated in FIG. 2, a recessed and protruding structure 20 is formed in the bottom surface of each well 10. The recessed and protruding structure 20 includes plural recessed portions 20a and plural protruding portions 20b adjacent to the recessed portions 20a. The recessed and protruding portions 20a and 20b are arranged periodically. In the sample analysis device 101, the sample analysis device 101 made of synthetic resin or the like itself serves as a base portion where the recessed and protruding structure 20 is formed.

The recessed and protruding portions 20a and 20b are approximately linear. The side surfaces of each of the recessed portions or protruding portions 20a and 20b are inclined. The recessed and protruding structure 20 may be configured so that the side surfaces of each recessed or protruding portion 20a or 20b may be approximately vertical to the surface of the sample analysis device 101.

As illustrated in the enlarged cross-sectional view of FIG. 3, the depth of the recessed portions 20a (the height of each protruding portion 20b) is indicated by H, and the width of the recessed portions 20a and the width of the protruding portions 20b are indicated by Wa and Wb, respectively, at a position of H/2 from the bottom surface. The position is indicated by a dot-and-dash line. The width Wa of the recessed portions 20a and the width Wb of the protruding portions 20b preferably satisfy a relationship of Wa>Wb.

When being made of synthetic resin, the sample analysis device 101 configured as described above can be easily produced by integral molding.

<Sample Analysis Device According to Second Embodiment>

Figure 4:
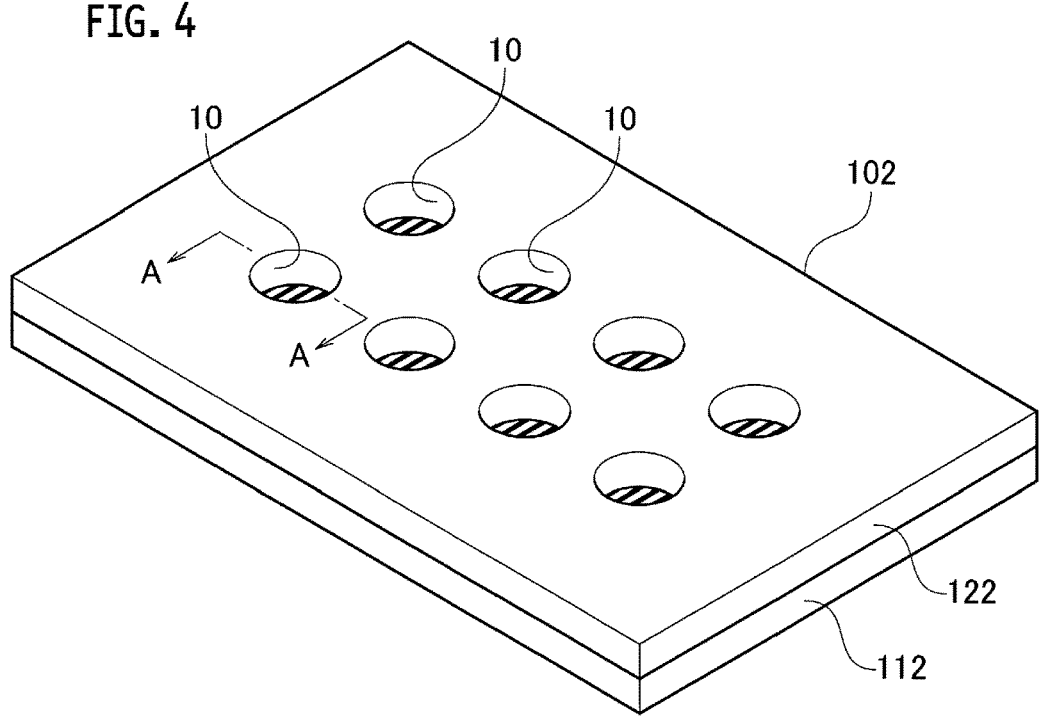
FIG. 4 is a perspective view illustrating a sample analysis device according to the second embodiment.
Figure 5:
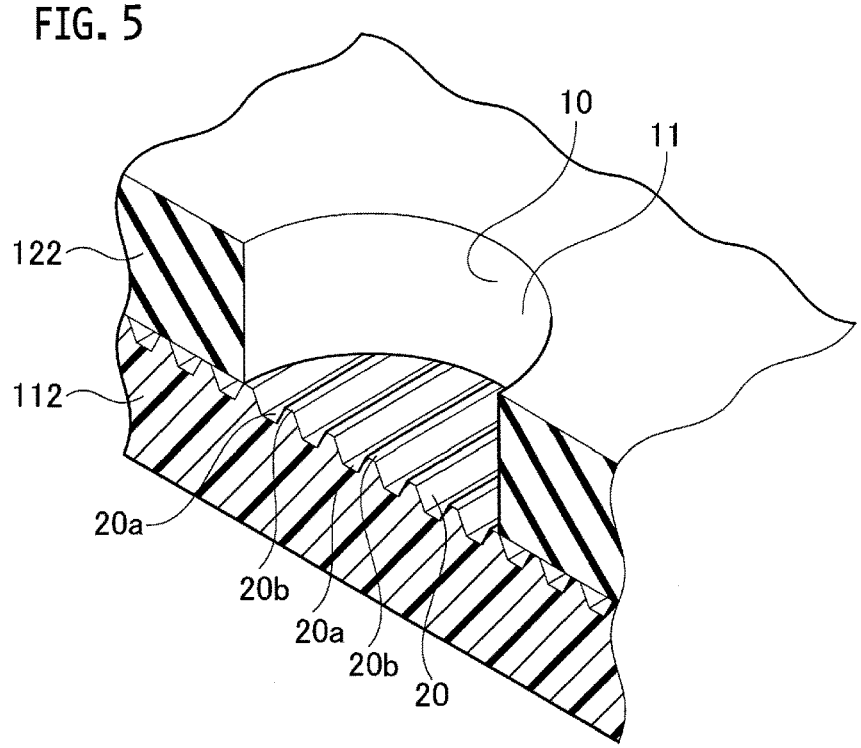
FIG. 5 is a partial enlarged perspective view taken along a line A-A of FIG. 4.

A description is given of the configuration of a sample analysis device according to the second embodiment with reference to FIGS. 4 and 5. In FIGS. 4 and 5, the portions substantially the same as those of FIGS. 1 to 3 are given the same reference numerals, and the description thereof is omitted.

In FIG. 4, a sample analysis device 102 according to the second embodiment includes a substrate 112, which is made of synthetic resin, for example, and a sheet 122, which is made of synthetic resin and laid on the substrate 112. The sheet 122 is silicone polymer sheet, for example, and is referred to as a silicone polymer sheet 122 hereinafter. The sample analysis device 102 is also rectangular but may have any external profile.

The material of the sheet laid on the substrate 112 is not limited to silicone polymer. The material of the sheet may be resin such as polystyrene, ABS or polycarbonate for example, which is a material cheaper than silicone polymer.

The sample analysis device 102 includes plural wells 10, which are cylindrical recesses, similar to the sample analysis device 101.

FIG. 5 illustrates an enlarged view of a cross-section taken along a line A-A of FIG. 4. As illustrated in FIG. 5, in the entire surface of the substrate 112, a recessed and protruding structure 20, which includes plural recessed and protruding portions 20a and 20b arranged, is formed. In the sample analysis device 102, the substrate 112 made of synthetic resin or the like serves as a base portion where the recessed and protruding structure 20 is formed.

In the sample analysis device 101 according to the first embodiment, the recessed and protruding structure 20 is formed only in the bottom surface of each well 10. On the other hand, in the sample analysis device 101 according to the second embodiment, the recessed and protruding structure 20 is formed on the entire surface of the substrate 112.

In the sample analysis device 102, cylindrical through-holes 11 are formed in the silicone polymer sheet 122. The silicone polymer sheet 122 including the through-holes 11 is laid on the substrate 112 to form the wells 10. When the substrate 112 is laid on the silicone polymer sheet 122, the sample analysis device 102 has substantially the same configuration as that of the sample analysis device 101, in which the recessed and protruding structure 20 is formed in the bottom surface of each well 10.

The silicone polymer sheet 122 tightly adheres to the substrate 112 and does not need to be bonded to the substrate 112. When the silicon polymer sheet 122 and substrate 112 are not bonded to each other, the silicone polymer sheet 122 can be peeled off if necessary in a later-described step to detect exosomes. It is certain that the silicone polymer sheet 122 may be bonded to the substrate 112.

The substrate 112 and silicone polymer sheet 122 may be configured to tightly adhere to each other with a packing interposed between the substrate 112 and silicone polymer sheet 122. The packing may be a plate which is made of silicone rubber and includes through-holes having approximately the same diameter as those of the through-holes 11 and are arranged at the same positions as the respective through-holes 11.

The packing may be a ring-shaped member having approximately a rectangular or circular cross section and may be provided for each through-hole 11.

The silicone polymer sheet 122 may be provided with ring-shaped protrusions, which are fitted into ring-shaped grooves provided for the packing. Alternatively, the silicone polymer sheet 122 may be provided with ring-shaped grooves, which are fitted on ring-shaped protrusions provided for the packing.

On the surface of the silicone polymer sheet 122 joined to the substrate 112, plural packing may be provided. The plural packing has approximately the same diameter as that of the through-holes 11. The plural packing is provided for the respective through-holes 11.

<Capturing Method for Exosomes According to an Embodiment>

A description is given of a capturing method for exosomes according to the embodiment using the sample analysis device 101 according to the first embodiment or the sample analysis device 102 according to the second embodiment. Herein, the description is given for the case of using the sample analysis device 101.

Figure 6:
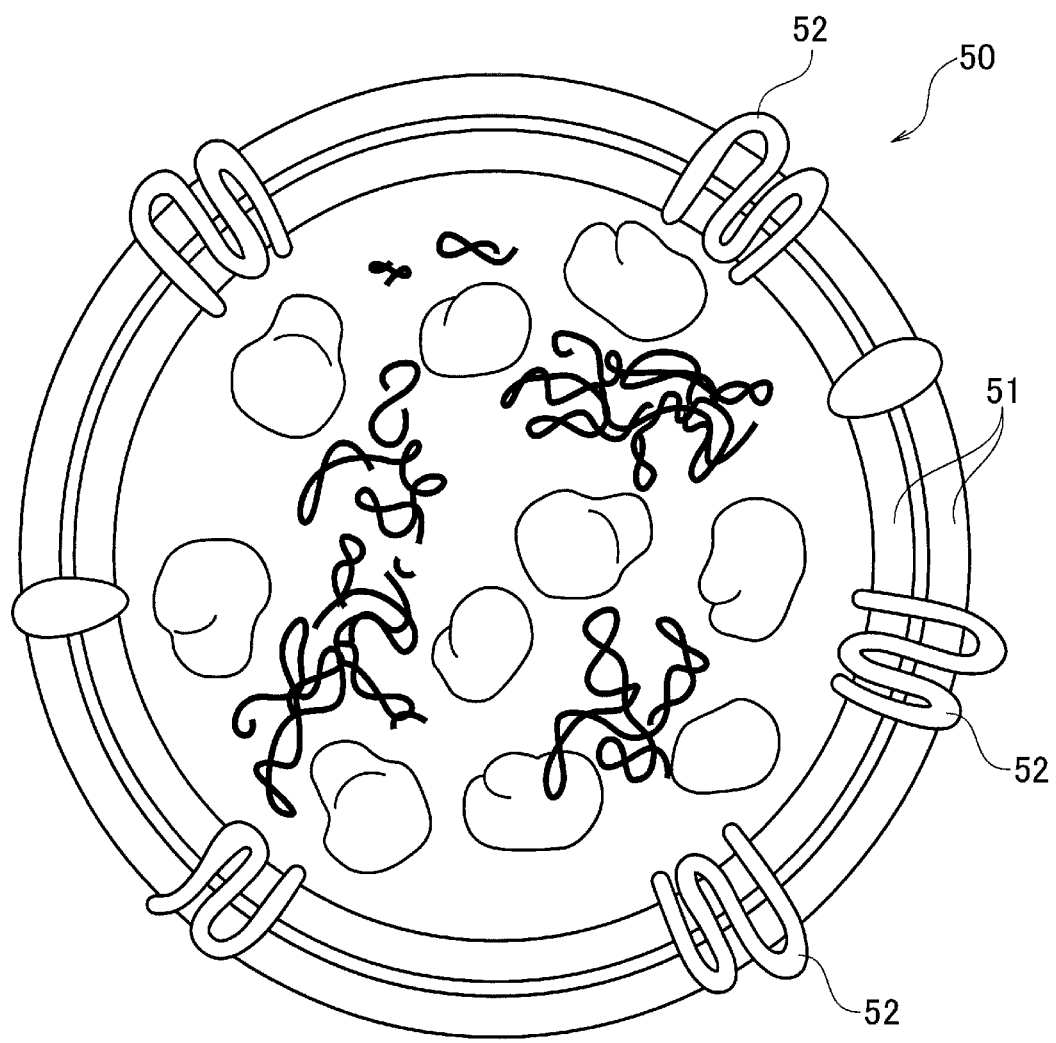
FIG. 6 is a schematic cross-sectional view of an exosome.

FIG. 6 is a schematic cross-sectional view of an exosome. The exosome illustrated in FIG. 6 is one of exosomes 50 which is a target to be detected. As illustrated in FIG. 6, each exosome 50 is covered with a lipid bilayer membrane 51. In the lipid bilayer membrane 51, plural transmembrane proteins 52 exist. The number of the membrane proteins 52 and the positions thereof in the lipid bilayer membrane 51 vary depending on the exosome type.

In Example 1, the exosomes 50 have an average particle diameter E of 100 nm. In Example 1, the widths Wa and Wb of the recessed and protruding portions 20a and 20b in the sample analysis device 101 are 240 nm and 80 nm, respectively. The depth H of the recessed portions 20a is 50 nm.

In Example 2, the average particle diameter E of the exosomes 50 is 70 nm. In Example 2, the widths Wa and Wb of the recessed and protruding portions 20a and 20b are 260 nm and 60 nm, respectively. The depth H of the recessed portions 20a is 60 nm.

The average particle diameter E of the exosomes 50 refers to an average of particle diameters of the exosomes 50 measured by any measurement method. Examples of the measurement method are wet-type measurement using nano-particle tracking to observe the exosomes 50 included in a solution and dry-type measurement using a transmission electron microscope to observe the exosomes 50 with the shape thereof unchanged.

In the latter measurement method, to observe the exosomes 50 in the dry-type measurement with the shape thereof unchanged, the sample containing the exosomes 50 is subjected to a treatment based on a method to observe cells.

To be specific, the sample is immobilized on a substrate and is then repeatedly impregnated with ethanol as the concentration thereof is increased step by step from the low-concentration ethanol to pure 100% ethanol. Water in the sample is thereby replaced with ethanol for dehydration.

Next, the sample is impregnated with a solution containing synthetic resin soluble in ethanol to replace ethanol in the sample with the synthetic resin. The sample with ethanol replaced with synthetic resin is cut into thin sections for observation.

The sample containing the exosomes 50 may be quickly frozen. The sample is thereby dehydrated and observed with the form of the exosomes 50 maintained.

The capturing method for exosomes according to the embodiment and the sample analysis method to detect the captured exosomes employ beads 70 (illustrated in (a) of FIG. 7) to detect the exosomes 50 as described later. In Examples 1 and 2, the beads 70 have a diameter D of 200 nm. The beads 70 are made of synthetic resin and are approximately spherical, for example.

FIG. 8 illustrates steps of the procedure to capture the exosomes 50 by the sample analysis device 101. In step S1 of FIG. 8, an operator who conducts the sample analysis dispenses a buffer solution F60 containing an appropriate amount of antibodies 60 into the wells 10 as illustrated in (a) of FIG. 9. CD63, CD9 and the like, which are transmembrane proteins, are known as antigens for identifying exosomes.

The antibodies 60 used in the step S1 are antibodies which react with the membrane proteins 52 as antigens. The antigens are not limited to the membrane proteins 52 and may be other substances existing on the surface of the lipid bilayer membrane 51.

In the step S1, the operator shakes the sample analysis device 101 which is in the state illustrated in (a) of FIG. 9 for an appropriate period of time using a shaking machine. By the processing of the step S1, the antibodies 60 are immobilized on the surface of the recessed and protruding structure 20. The step S1 is an antibody immobilization step.

In step S2, the operator discards the buffer solution F60 containing the antibodies and washes the wells 10 with a buffer solution.

(a) of FIG. 10 schematically illustrates the state of the surface of the recessed and protruding structure 20 after the step S2. The antibodies 60 tightly adhere to the surface by hydrophobic bonding. The method to immobilize the antibodies 60 to the surface of the recessed and protruding structure 20 is not limited to hydrophobic bonding. The antibodies 60 may be immobilized to the surface of the recessed and protruding structure 20 by chemically modifying the surface of the recessed and protruding structure 20 appropriately for covalent bonding or the like. The method to immobilize the antibodies 60 to the surface of the recessed and protruding structure 20 is just a method generally used in immunoassay.

In order to prevent the antigens from being non-specifically adsorbed to other than the antigen recognition site of the antibodies 60, in step S3, the operator performs blocking for the surface of the recessed and protruding structure 20. To be specific, the operator dispenses fat-free milk diluted with a buffer solution into the wells 10 and shakes the sample analysis device 101 for a predetermined period of time in a similar manner to the step S1.

Fat-free milk contains proteins which cannot adhere to the exosomes 50 and is suitable for blocking. The substance used for blocking is not limited to fat-free milk and can be any substance that has a similar effect.

In step S4, the operator discards the buffer solution containing the fat-free milk and washes the well 10 with a buffer solution. The buffer solution used in the washing does not always need to contain fat-free milk. The washing may be omitted. As schematically illustrated in (b) of FIG. 10, a block layer 65 is formed on the surface of the recessed and protruding structure 20 by the steps S3 and S4.

Next, in step S5, the operator dispenses a sample solution F50 containing the exosomes 50 to be detected into the wells 10 as illustrated in (b) of FIG. 9 and shakes the sample analysis device 101 for an appropriate period of time in a similar manner to the step S1. In the step S5, the operator shakes the sample analysis device 101 for about two hours, for example.

By the step S5, many of the exosomes 50 contained in the sample solution F50 are immobilized in the recessed portions 20a of the recessed and protruding structure 20 because of antigen-antibody reaction between the antibodies 60 and membrane proteins 52. The step S5 is an exosome immobilization step.

After the step S5, the operator discards the sample solution F50 and washes the wells 10 with a buffer solution in step S6. Washing of the wells 10 with the buffer solution can remove the exosomes 50 adhering to the surface of the recessed and protruding structure 20 by a non-specific adsorption instead of antigen-antibody reaction.

(c) of FIG. 10 illustrates a state where one exosome 50 is immobilized to one of the recessed portions 20a. The exosomes 50 in (c) of FIG. 10 are schematically illustrated by simplifying the exosome 50 illustrated in FIG. 6. In the example illustrated in (c) of FIG. 10, each exosome 50 includes two types of membrane proteins 52 which are schematically indicated by ellipse lines and hatched ellipses.

As illustrated in (c) of FIG. 10, one of the antibodies 60 binds to one of the membrane proteins 52 (indicated by the hatched ellipses) by antigen-antibody reaction, so that the exosome 50 of interest is immobilized in the recess 20a. The number of types of the membrane proteins 52 is not limited to two. Substances different from the membrane proteins may be used as an antigen as described above. In the case of using two types of monoclonal antibodies to recognize and capture the exosomes 50, it is necessary to recognize one or two types of membrane proteins 52.

As illustrated in (b) of FIG. 7, antibodies 80 are immobilized to the surface of each bead 70 in advance. The step to immobilize the antibodies 80 to the bead 70 with no antibodies 80 immobilized thereto (illustrated in (a) of FIG. 7) as illustrated in (b) of FIG. 7 may be performed in a different step from the series of steps shown in FIG. 8.

In step S7, the operator dispenses a buffer solution F70 containing the beads 70 with the antibodies 80 immobilized to the surfaces thereof as illustrated in (c) of FIG. 9 and shakes the sample analysis device 101 for an appropriate period of time in a similar manner to the step S1.

By the step S7, as illustrated in (d) of FIG. 10, the exosomes 50 are modified with the beads 70. By modifying the exosomes 50 with the beads 70, the beads 70 are used as labels for the exosomes 50. The step S7 is a modification step to modify the exosomes 50 with the beads 70.

In step S8, the operator discards the buffer solution F70 and washes the wells 10 with a buffer solution. The exosomes 50 can be thus captured by the sample analysis device 101 and can be modified with the beads 70.

In the embodiment, the antibodies 80, which are different from the antibodies 60 immobilized to the surface of the recessed and protruding structure 20, are immobilized to the beads 70. The antibodies 80 bind to the membrane proteins 52 indicated by the white ellipses by the antigen-antibody reaction, and the beads 70 are therefore immobilized to the exosomes 50.

When the antibodies immobilized to the surface of the recessed and protruding structure 20 are different from the antibodies immobilized in the surfaces of the beads 70, exosomes having two different types of antigens can be detected. It is certain that the same type of antibodies 60 as that of the antibodies 60 immobilized in the surface of the recessed and protruding structure 20 may be immobilized to the beads 70. Whether to use the same type of antibodies or different types of antibodies can be properly selected depending on the convenience of the sample analysis.

In the above description, the exosomes 50 are captured in the recessed portions 20a of the recessed and protruding structure 20 first, and the beads 70 are then injected to be immobilized to the exosomes 50. However, the exosomes 50 and beads 70 may be simultaneously put into a buffer solution for reaction as another procedure. In this case, the immobilization reaction between the exosomes 50 and beads 70 is conducted in the solution, thus providing an advantage of increasing the reaction rate thereof.

The beads 70 may be configured to include a magnetic substance such as ferrite. Such beads 70 including a magnetic substance can be quickly collected by providing a magnet on the lower surface of the sample analysis device 101 in the step S7. Moreover, the beads 70 can be effectively directed to the recessed portions 20a by the magnetic field. This can shorten the time taken to conduct the step S7.

By simultaneously injecting the exosomes 50 and beads 70 as described above, the reaction can be further accelerated also in the aforementioned case. The shaking time taken to immobilize the exosomes 50 to the recessed and protruding structure 20 can be shortened to a couple of minutes.

After the beads 70 are attracted by the magnetic field, the power supply to the magnet provided on the lower surface of the sample analysis device 101 is turned off in the case of an electromagnet, or is moved away from the sample analysis device 101 in the case of a permanent magnet. The buffer solution F70 is then stirred again. Some of the beads 70 which are immobilized in any manner other than the antigen-antibody reaction are once removed from the recessed and protruding structure 20 and are then attracted again by the magnetic field. This can increase the reaction yield.

In the case of using the beads 70 including a magnetic substance, the beads 70 can be stirred by changing the direction and strength of the magnetic field thereof instead of shaking.

The exosomes 50 can be flattened by force generated by the beads 70 due to the magnetic field. However, once the exosomes 50 are captured by the recessed portions 20a, the exosomes 50 do not move to the protruding portions 20b. Accordingly, such deformation cannot influence detection of the exosomes 50.

In FIG. 8, the sample solution F50 containing the exosomes 50 and the buffer solution F70 containing the beads 70 are separately dispensed into the wells 10. However, the sample containing the exosomes 50 and the beads 70 may be simultaneously put into a buffer solution, and the mixture is dispensed into the wells 10. The steps S5 and S7 are thus performed simultaneously. The beads 70 can be beads including a magnetic substance also in this case.

Preferably, in the sample analysis devices 101 and 102 according to the first and second embodiments, it is preferable that the average particle diameter E of the exosomes 50, the diameter D of the beads 70, the widths Wa and Wb of the recessed and protruding portions 20a and 20b of the recessed and protruding structure 20, the depth H of the recessed portions 20a have a relationship shown below.

When the dimensional profiles of the sample analysis devices 101 and 102, the exosomes 70 to be detected, and the beads 70 used as the labels have a relationship shown below, as illustrated in (d) of FIG. 10, it is more likely that one bead 70 binds to one exosome 50. The quantity relationship between the exosomes 50 and the beads 70 can be as close to 1:1 as possible.

Preferably, the width Wa of the recessed portions 20a is larger than the average particle diameter E of the exosomes 50 and is smaller than twice the diameter D of the beads 70. That is, it is preferable that the sample analysis devices 101 and 102 have a relationship of Expression (1):

$$E<Wa<2D \tag{1}$$

When the sample analysis devices 101 and 102 satisfy E<Wa in Expression (1), the exosomes 50 can be immobilized in the recessed portions 20a. When the sample analysis devices 101 and 102 satisfy Wa<2D in Expression (1), it is less likely that two beads 70 enter any one of the recessed portions 20a abreast in the width direction of each recess 20a. Accordingly, the quantity relationship between the exosomes 50 and beads 70 becomes close to 1:1.

It is preferable that the sample analysis devices 101 and 102 satisfy Expression (2):

$$Wb<D<Wa<2D \tag{2}$$

When Wb<D in Expression (2) is satisfied, the beads 70 are less likely to be located on the protruding portions 20b. When D<Wa in Expression (2) is satisfied, the beads 70 can enter the recess 20a.

It is preferable that the sample analysis devices 101 and 102 satisfy Expression (3):

$$Wb<E \tag{3}$$

When Expression (3) is satisfied, the exosomes 50 are less likely to be located on the protruding portions 20b.

It is preferable that the sample analysis devices 101 and 102 satisfy Expression (4):

$$E<Wa<4E \tag{4}$$

Thus, in this non-limiting example, the recessed portion has a width Wa smaller than four times the average particle diameter E of the exosomes 50.

Most of the spherical exosomes 50 captured in the recessed portions 20a deform so that the area of contact between each exosome 50 and the corresponding recess 20a increases as illustrated in (c) of FIG. 10. As described above, using the beads 70 including a magnetic substance accelerates deformation of the exosomes 50 because of the magnetic field.

It is assumed that a spherical exosome 50 deforms to an ellipsoid with constant volume. When the diameter of the sphere changes by 50%, the diameter of the contact site between the exosome 50 and recess 20a, which is the long side of a spheroid, increases by about 40%. Moreover, the exosome 50 actually deforms so that the contact site between the exosome 50 and recess 20a is larger than that of the spheroid. The diameter of the contact site can increase by 50% or more of the diameter of the original sphere, or by 100% or more in some cases.

Consequently, it is preferable that Wa<4E of Expression (4) is satisfied.

The average particle diameter E of the exosomes 50 and the diameter D of the beads 70 preferably satisfy Expression (5):

$$E<D \quad (5)$$

When Expression (5) is satisfied, the exosome 50 immobilized in each recess 20a is less likely to be modified with plural beads 70, and the quantity relationship between the exosomes 50 and beads 70 can be close to 1:1. When Expression (5) is satisfied, the exosomes 50 are more likely to reactively come into the beads 70, resulting in an increase in the reaction yield.

The depth H of the recessed portions 20a preferably satisfies Expression (6):

$$(D+E)/8<H \quad (6)$$

When Expression (6) is satisfied, the exosomes 50 are substantially reliably immobilized in the recessed portions 20a, and the beads 70 are prevented from being non-specifically adsorbed into the protruding portions 20b. The beads 70 are thereby substantially reliably immobilized to the exosomes 50 existing in the recessed portions 20a.

More preferably, the depth H of the recessed portions 20a satisfies Expression (7):

$$(D+E)/6<H \quad (7)$$

Example 1 satisfies Expressions (1) to (6), and Example 2 satisfies Expressions (1) to (7). According to Examples 1 and 2, the quantity relationship between the exosomes 50 and beads 70 which are immobilized to the recessed portions 20a is substantially 1:1. A very few of the exosomes 50 each bind to a couple of beads 70, but rarely influence quantitative detection of the exosomes 50.

Most preferably, all of Expressions (1) to (7) are satisfied. However, it is only necessary to satisfy some of Expressions (1) to (7). It is even effective if only Expression (1) is satisfied. It is preferable that Expression (4) is satisfied in addition to Expression (1). It is also preferable that Expression (3) is satisfied in addition to Expression (1). It is more preferable that Expression (3) and (4) are satisfied in addition to Expression (1).

It is preferable that Wb<D in Expression (2) is satisfied in addition to Expression (1). It is more preferable that Expression (4) and Wb<D in Expression (2) are satisfied in addition to Expression (1). It is also more preferable that Expression (3) and Wb<D in Expression (2) are satisfied in addition to Expression (1). It is still more preferable that all of Expressions (1), (3), and (4) and Wb<D in Expression (2) are satisfied.

The sample analysis device may have a circular disc shape in addition to a rectangular shape illustrated in FIGS. 1 and 4 as the sample analysis devices 101 and 102. The reaction using the above-described immunoassay can be also conducted in a similar manner with the disc-shaped sample analysis device. When the sample analysis device has a circular disc shape, the recessed portions 20a and protruding portions 20b of the recessed and protruding structure 20 may be spiral or concentric. The disc shape can be effective at a later-described detection of the exosomes 50.

When the sample analysis device has a disc shape, it is possible to provide a liquid-feeding channel structure corresponding to the disc shape. Using FIGS. 11 to 13, such a disc-shaped sample analysis device provided with the liquid-feeding channel structure is described as a sample analysis device according to the third embodiment. In the description of the third embodiment, the substances and portions substantially the same as those of the first and second embodiments are given the same reference numerals.

<Sample Analysis Device of Third Embodiment>

In FIG. 11, a sample analysis device 103 according to the third embodiment is formed into a disc shape having the same diameter as that of optical discs, such as Blu-ray discs, DVDs, and compact discs. The sample analysis device 103 is a sample analysis disc. FIG. 11 is a plan view of the sample analysis device 103 seen from a transparent protecting layer 36.

The sample analysis device 103 is made of synthetic resin such as polycarbonate similarly to optical discs.

At the center of the sample analysis device 103, a circular opening 103a is formed. Around the opening 103a, injection holes 31, into which a sample containing the exosomes 50 to be detected is dropped, are formed so as to surround the opening 103a.

The injection holes 31 are connected to respective channels 32 through which the sample is flown. The plural channels 32 extend radially from the respective injection holes 31 toward the peripheral edge of the sample analysis device 103. In the middle of each channel 32, a bead filled portion 33, which is filled with the beads 70, is provided.

In the peripheral edge of the sample analysis device 103, fan-shaped detection regions 34 are provided. The channels 32 are connected to the respective detection regions 34. When the sample is injected through the injection holes 31 and the sample analysis device 103 is rotated, the sample is transmitted through the channels 32 and reaches the respective detection regions 34. The detection regions 34 serve as injection portions to which each solution is injected through the injection holes 31 and channels 32.

As illustrated in (a) of FIG. 12, the recessed and protruding structure 20, which includes spiral or concentric recessed and protruding portions 20a and 20b, is formed in the peripheral edge of the sample analysis device 103. The detection regions 34 are provided within the recessed and protruding structure 20.

As illustrated in (b) of FIG. 12, the recessed and protruding structure 20 illustrated in (a) of FIG. 12 may be replaced with a pit structure 20P which includes plural recessed pits 20c arranged in a spiral or concentric fashion. The part of the pit structure 20P other than the pits 20c is protruded relative to the pits 20c. The pit structure 20P therefore serves as a recessed and protruding structure.

In the sample analysis device 103, the disc portion which is made of synthetic resin or the like and is provided on the opposite side to the transparent protecting layer 36 serves as a base portion constituting the recessed and protruding structure 20 (including the pit structure 20P).

As illustrated in FIG. 11, the portions of the recessed and protruding structure 20 other than the detection regions 34 serve as track regions 35. When address information is provided for the track regions 35, radial and circumferential positions in the sample analysis device 103 can be specified. Such address information may be provided in the form of pits or embosses or may be expressed by wobbling on the side surfaces of the recessed and protruding portions 20a and 20b.

FIG. 13 is a partial cross-sectional view of the sample analysis device 103. The beads 70 which are packed in the bead filled portion 33 are immobilized to the antibodies 80 in advance in a similar manner to (b) of FIG. 7. Actually, a reflective layer reflecting a laser beam is provided adjacent to the recessed and protruding structure 20 but is not illustrated in FIGS. 12 and 13.

First, the buffer solution F60 containing the antibodies 60 is injected through the injection holes 31 and the sample analysis device 103 is rotated, the antibodies 60 are immobilized to the surface of the recessed and protruding structure 20 similarly to (a) of FIG. 10. The surface of the recessed and protruding structure 20 may be subjected to blocking if necessary.

When the sample solution F50 containing the exosomes 50 to be detected is injected through the injection holes 31 and the sample analysis device 103 is rotated, the exosomes 50 are modified with the beads 70 as passing through the bead filled portions 33. The exosomes 50 modified with the beads 70 are immobilized in the recessed portions 20a in a similar manner to (d) of FIG. 10. FIG. 13 does not illustrate the exosomes 50 and only illustrates the beads 70 for convenience of illustration.

The detection regions 34 are irradiated through the transparent protecting layer 36 with a laser beam which is emitted from a laser beam source of a not-shown optical pickup and collected by an objective lens 40. The reflection of the irradiated laser beam is analyzed for detection of the beads 70 immobilized to the recessed portions 20a.

The dimensional relationship between the dimensional profile of the recessed and protruding structure 20 in the sample analysis device 103 according to the third embodiment and the exosomes 50 to be detected or the beads 70 used as the labels is the same as that of the first and second embodiments.

<Exosome Detection and Sample Analysis Method>

Next, a description is given of a detection method to detect the exosomes 50 captured as illustrated in (d) of FIG. 10 by the sample analysis devices 101 to 103 according to the first to third embodiments.

A first detection method is to detect the beads 70 using an optical microscope and count the detected beads 70 by using image processing. The exosomes 50 can be therefore quantitatively detected. The first detection method is suitable for detecting the exosomes 50 captured by the sample analysis devices 101 and 102 according to the first and second embodiments.

The beads 70 may be counted in a large area by moving the stage on which the sample analysis devices 101 and 102 are mounted. This can increase the measurement accuracy. The optical microscope may be replaced with a laser microscope. This can increase the detection resolution and increase the S/N ratio.

In a second detection method, the beads 70 are designed to include a fluorescent substance which produces fluorescence upon irradiation of light of a specific wavelength. The beads 70 are counted by detecting the fluorescence. The beads 70 which produce fluorescence may be counted using an optical microscope. Alternatively, the beads 70 may be counted by detecting the total amount of fluorescence with an optical sensor. The second detection method is suitable for detecting the exosomes 50 captured by the sample analysis devices 101 and 102 according to the first and second embodiments.

In the case of using the first and second detection methods, the beads 70 may be detected from the back side of the sample analysis device 101 or 102 where the wells 10 are not provided. Such a configuration can prevent mechanical interference between the detection apparatus and the sample analysis device 101 or 102. Moreover, the shape of the wells 10 may be designed so as to prevent interference with a microscope objective lens and the like.

In the case of the sample analysis device 102 according to the second embodiment, the silicone polymer sheet 122 may be removed. When the silicone polymer sheet 122 is removed, detection of the beads 70 is performed with only the substrate 112. It is therefore possible to prevent the mechanical interference with the detection device.

In a third detection method, the beads 70 can be detected and counted by using secondary antibodies labeled with an enzyme which specifically binds to the antibodies 80 immobilized to the beads 70. Representative secondary antibodies are horseradish perioxidaze (HRP) labeled antibodies and Alkaline Phosphatase (AP) labeled antibodies.

These secondary antibodies cause chemiluminescence with the addition of a chemiluminescent substrate corresponding to the enzyme. The beads 70 can be counted by modifying the beads 70 immobilized to the exosomes 50 with the secondary antibodies and detecting an amount of chemiluminescence caused by adding the chemiluminescent substrate.

As a fourth method, in the case of the sample analysis device 103 according to the third embodiment, the beads 70 can be counted by scanning the sample analysis device 103 with a laser beam emitted from the laser light source of the optical pickup as described above. The beads 70 can be counted at high speed and high accuracy by moving the spot of the laser beam along the recessed portions 20a of the recessed and protruding structure 20 as tracks with a servo mechanism.

By counting the beads 70 immobilized to the exosomes 50 as the labels as described above, the exosomes 50 can be quantitatively measured at high accuracy for analyzing the sample.

As stated above, according to the sample analysis device and capturing method for exosomes according to the embodiments, exosomes are detected with high accuracy.

The present invention is not limited to the embodiments described above and can be variously changed without departing from the scope of the invention.

What is claimed is:

1. A sample analysis device, comprising:
   a base portion;
   a recessed portion which is formed on the base portion and in which an antibody that binds to an antigen existing on a surface of each of a plurality of exosomes to be detected is immobilized and then caused to bind to the exosomes, wherein said exosomes have an average particle diameter of around 100 nm; and
   a protruding portion adjacent to the recessed portion,
   wherein the recessed portion and the protruding portion are periodically arranged on the base portion,
   wherein the protruding portion has a width smaller than the average particle diameter of the exosomes,
   and wherein the recessed portion has a width smaller than four times the average particle diameter of the exosomes.

2. The sample analysis device according to claim 1, wherein the recessed portion has a width larger than the average particle diameter of the exosomes and is smaller than twice a diameter of beads modifying the exosomes.

3. A sample analysis device, comprising:
   a base portion;

a recessed portion which is formed on the base portion and in which an antibody that binds to an antigen existing on a surface of each of a plurality of exosomes to be detected is immobilized and then caused to bind to the exosomes, said exosomes having an average particle diameter of 100 nm; and a protruding portion adjacent to the recessed portion, wherein the recessed portion and the protruding portion are periodically arranged on the base portion, wherein the protruding portion has a width smaller than a diameter of beads modifying the exosomes, and wherein the recessed portion has a width smaller than four times the average particle diameter of the exosomes.

4. The sample analysis device according to claim 3, wherein the recessed portion has a width larger than an average particle diameter of the exosomes and is smaller than twice the diameter of the beads.

* * * * *